United States Patent
Peltola et al.

(10) Patent No.: US 12,157,013 B2
(45) Date of Patent: Dec. 3, 2024

(54) METHOD AND APPARATUS TO OPTIMIZE A RADIATION TREATMENT PLAN USING HIERARCHICALLY-DIVERSIFIED PLANNING TEMPLATES

(71) Applicant: Siemens Healthineers International AG, Steinhausen (CH)

(72) Inventors: Jarkko Y. Peltola, Tuusula (FI); Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 245 days.

(21) Appl. No.: 17/954,642

(22) Filed: Sep. 28, 2022

(65) Prior Publication Data

US 2024/0100358 A1   Mar. 28, 2024

(51) Int. Cl.
  *A61N 5/10*      (2006.01)
  *G16H 20/40*     (2018.01)
  *G16H 70/20*     (2018.01)

(52) U.S. Cl.
  CPC .............. *A61N 5/103* (2013.01); *G16H 20/40* (2018.01); *G16H 70/20* (2018.01)

(58) Field of Classification Search
  CPC .......... A61N 5/10; A61N 5/103; G16H 20/40; G16H 70/20
  See application file for complete search history.

(56) References Cited

U.S. PATENT DOCUMENTS

| | | |
|---|---|---|
| 2007/0078306 A1 | 4/2007 | Allison et al. |
| 2018/0085596 A1 | 3/2018 | Peltola et al. |
| 2022/0001205 A1 | 1/2022 | Nord et al. |

FOREIGN PATENT DOCUMENTS

| | | |
|---|---|---|
| EP | 4176926 A1 | 5/2023 |
| WO | 2023083637 A1 | 5/2023 |

OTHER PUBLICATIONS

Cilla, Savino et al.; Template-based automation of treatment planning in advanced radiotherapy: a comprehensive dosimetric and clinical evaluation; Scientific Reports, vol. 10, No. 1, Jan. 16, 2020, XP093104371, DOI: 10.1038/s41598-019-56966-y; Retrieved from the Internet: URL:https://www.nature.com/articles/s41598-019-56966-y>; 13 pages.

(Continued)

*Primary Examiner* — Jurie Yun
(74) *Attorney, Agent, or Firm* — Fitch, Even, Tabin & Flannery LLP (57) ABSTRACT

A control circuit accesses a memory having stored therein a plurality of hierarchically-diversified radiation treatment planning templates. These templates include at least a first radiation treatment planning template that specifies radiation treatment planning information at a first hierarchical level. These templates also include at least a second radiation treatment planning template that specifies radiation treatment planning information at a second hierarchical level, wherein the second hierarchical level is more granular than the first hierarchical level. By one approach, the control circuit may access a plurality of differing ones of the second radiation treatment planning templates wherein each such template specifies radiation treatment planning information at the second hierarchical level. The control circuit is configured to optimize a radiation treatment plan for a given patient using a given radiation treatment facility as a function of at least the first and the second radiation treatment planning template.

20 Claims, 4 Drawing Sheets

(56) References Cited

OTHER PUBLICATIONS

International Search Report from related International Application No. PCT/EP2023/074887 dated Dec. 6, 2023; 6 pages.

METHOD AND APPARATUS TO OPTIMIZE A RADIATION TREATMENT PLAN USING HIERARCHICALLY-DIVERSIFIED PLANNING TEMPLATES

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and calculating a likely corresponding treatment result (such as a level of dosing) to identify a given set of treatment parameters that represent a good compromise between the desired therapeutic result and avoidance of undesired collateral effects.

Plan creation can be based, at least in part, upon use of template specifications. Such templates often include expert-created rules describing how planning should be done to help achieve a reliably predicted outcome. While undoubtedly helpful, the use of such templates is not always without issue.

BRIEF DESCRIPTION OF THE DRAWINGS

The above needs are at least partially met through provision of the method and apparatus to optimize a radiation treatment plan using hierarchically-diversified planning templates described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments, a control circuit accesses a memory having stored therein a plurality of hierarchically-diversified radiation treatment planning templates. These templates include at least a first radiation treatment planning template that specifies radiation treatment planning information at a first hierarchical level. These templates also include at least a second radiation treatment planning template that specifies radiation treatment planning information at a second hierarchical level, wherein the second hierarchical level is more granular than the first hierarchical level. By one approach, the control circuit may access a plurality of differing ones of the second radiation treatment planning templates wherein each such template specifies radiation treatment planning information at the second hierarchical level. The control circuit is configured to optimize a radiation treatment plan for a given patient using a given radiation treatment facility as a function of at least the first and the second radiation treatment planning template.

By one approach, the foregoing hierarchical levels correspond to sequentially different steps in planning the radiation treatment plan. For example, one such sequentially different step can comprise a field geometry selection step while another of the sequentially different steps comprises an iterative radiation treatment plan optimization step. By one approach, the radiation treatment planning information for each of the first and second hierarchical levels comprises initial planning information corresponding to planning the radiation treatment plan.

By one approach, the aforementioned first hierarchical level corresponds to universally-applied specifications for the given treatment facility while the aforementioned second hierarchical level corresponds to specifications that are not universally applied for the given radiation treatment facility.

By one approach, the aforementioned second radiation treatment planning template corresponds to specifications as per one of per fractionation, per prescribing physician, and per radiation treatment machine planning workflow.

These teachings are flexible in practice and will accommodate, for example, having information in the second radiation treatment planning template comprise information that is identical to information in the first radiation treatment planning template. As another example, the second radiation treatment planning template can include information that supplements information in the first radiation treatment planning template. And as yet another example, the second radiation treatment planning template can include information that overrides information in the first radiation treatment planning template.

So configured, these teachings can readily accommodate and permit a given radiation treatment facility to provide and use multiple planning objectives for various fractionations, treatment devices and platforms, and even personal preferences for individual oncologists. These teachings can also greatly ease challenges faced when seeking to update and/or refine template-based information.

Figure 1:
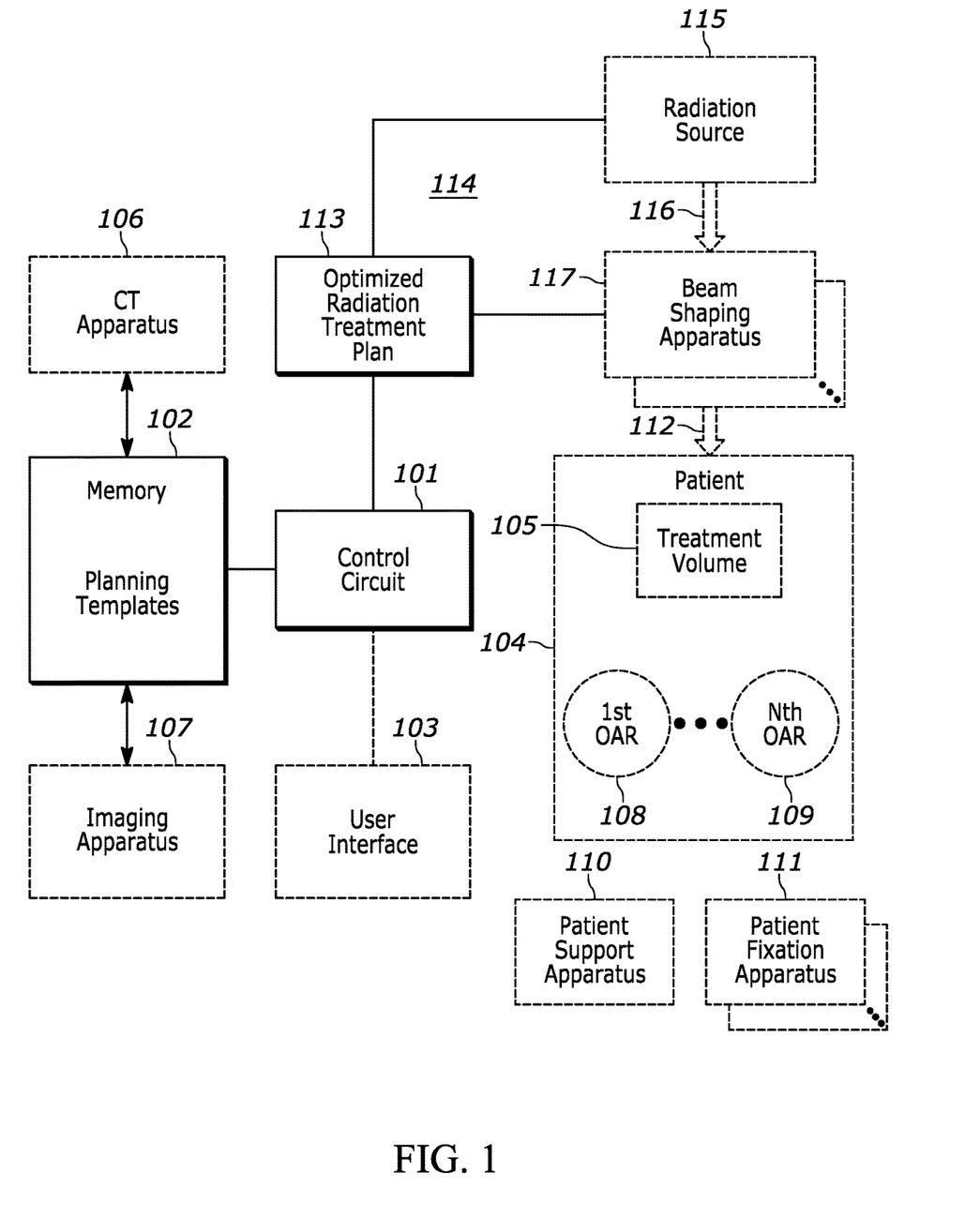
FIG. 1 comprises a block diagram as configured in accordance with various embodiments of these teachings.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient, information regarding a particular radiation treatment platform as described herein, and planning templates as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
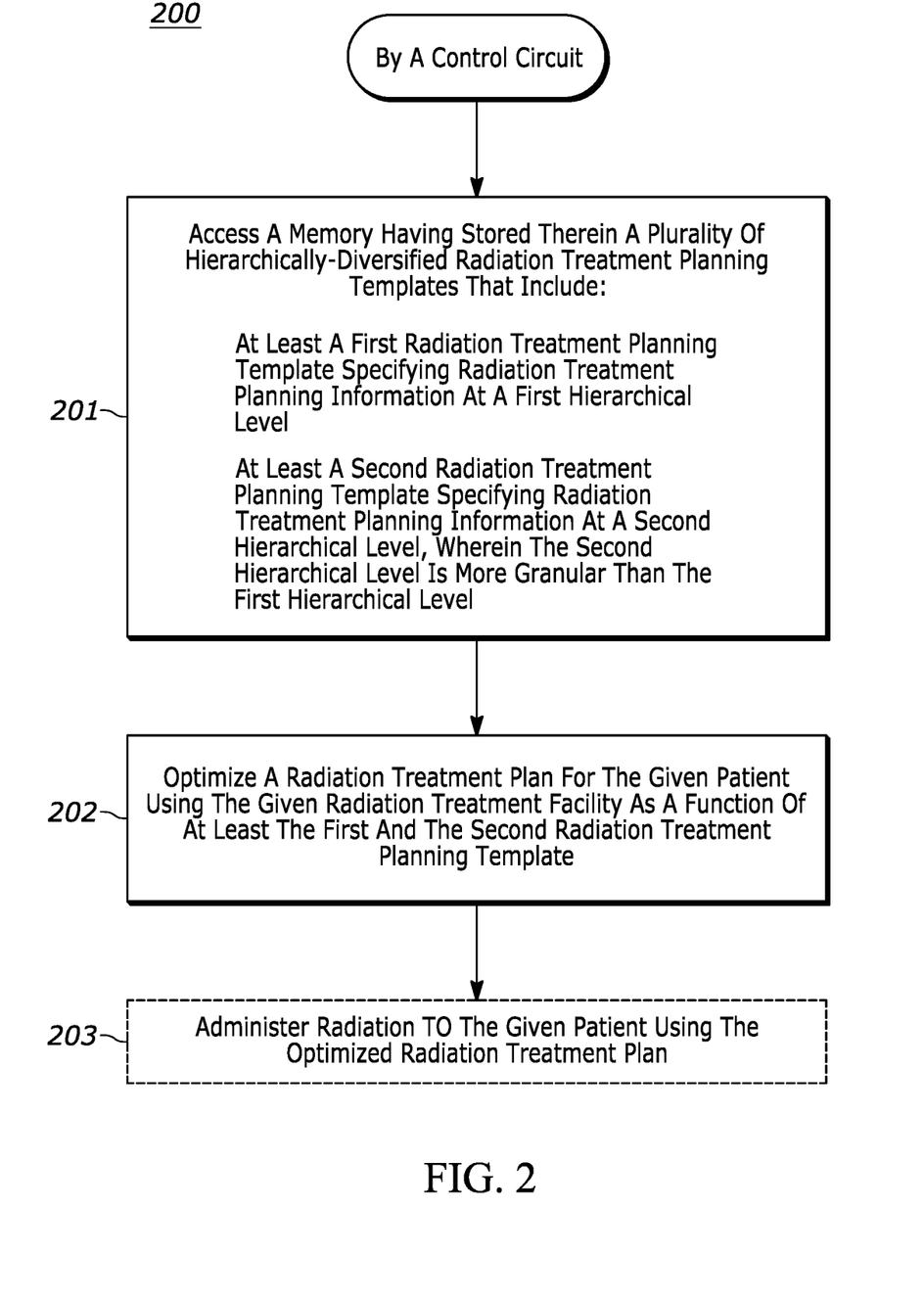
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized radiation treatment plan 113 to thereby facilitate treating a particular patient with therapeutic radiation using a particular radiation treatment platform per that optimized radiation treatment plan.

At block 201, the control circuit 101 accesses the aforementioned memory 102, the latter having a plurality of hierarchically-diversified radiation treatment planning templates stored therein. In a typical application setting a given template will comprise a data file. For many application settings, the radiation treatment planning information for each of these templates can comprise initial planning information corresponding to a radiation treatment plan. Examples of initial planning information include, but are not limited to, dosing targets and/or limits, multileaf collimator settings, critical organ delineations and associated dosimetrical goals, information about needed additional optimization structures, prescription and fractionation scheme information, field geometry specifications (including treatment technic selection regarding, for example, volumetric modulated arc therapy, intensity-modulated radiation therapy, 3-dimensional conformal therapy), treatment delivery strategy (such as image guided and/or breath-hold schemes), and so forth.

The specific information contained in a given template can vary but may include, for example, one or more optimization objectives. Optimization objectives can, for example, provide a measure by which the process can test or assure that a particular specified dose is being uniformly administered through the patient's target volume while avoiding undue dosing of other patient tissues (or, in other cases, that a series of dose histograms that specify acceptable dosing ranges for a variety of locations both in and external to the target volume are met).

Accordingly, optimization objectives will be understood to be objectives that are very much specifically designed to reflect and accommodate the technical details and specifications of a particular radiation treatment platform, specific details regarding the patient's presentation, and/or other physical details pertaining to a particular application setting. Such details are generally viewed as being outside the expertise and knowledge base of the person who prescribes the radiation treatment in the first place (i.e., for example, a licensed oncologist). As a result, the person prescribing the radiation treatment ordinarily does not also create the optimization objectives.

By one approach, at least some of (and, if desired, all of) the aforementioned hierarchical levels each correlates to sequentially different steps in planning the radiation treatment plan. For example, one of the sequentially different steps can comprise a field geometry selection step while another of the sequentially different steps comprises an iterative radiation treatment plan optimization step.

By one approach, at least one of the plurality of hierarchically-diversified radiation treatment planning templates comprises a first radiation treatment planning template that specifies radiation treatment planning information at a first hierarchical level. In addition, at least a second one of the plurality of hierarchically-diversified radiation treatment planning templates specifies radiation treatment planning information at a second hierarchical level that is more granular than the first hierarchical level. As used herein, the word "granular" will be understood to refer to information that is more specific by way of comparison (including but not limited to being more specific by way of additional and/or more precise details), as well as information that is contrary by way of comparison. That granularity may pertain, for example, to specifications as per fractionation, prescribing physician, and/or per radiation treatment machine planning workflow, to note but a few examples in these regards. (These teachings will accommodate having more than one radiation treatment planning template containing radiation treatment planning information at the first hierarchical level. These teachings will also accommodate accessing a plurality of differing ones of the second radiation treatment planning templates that each specify radiation treatment planning information at the second hierarchical level.)

As one example of hierarchical diversity, the aforementioned first hierarchical level can correspond, if desired, to universally-applied specifications for a given radiation treatment facility. The second hierarchical level, by way of contrast, can correspond to specifications that are not universally applied for that given radiation treatment facility.

By one approach, a given second radiation treatment planning template can include information that is identical to information in a given one of the first radiation treatment planning templates. That said, such a second radiation treatment planning template can also include information that supplements the information that is identical to that first radiation treatment planning template. Or, if desired, such a second radiation treatment planning template can include information that overrides information that is otherwise present in that first radiation treatment planning template. It should therefore be understood that a second radiation treatment planning template may include information that is identical to information found in a first radiation treatment planning template along with other information that supplements and/or overrides such information as found in that first radiation treatment planning template.

At block 202, the control circuit 101 optimizes a radiation treatment plan for the given patient using the given radiation treatment facility as a function of at least the aforementioned first and second radiation treatment planning template. There are various approaches to optimizing a radiation treatment plan. As these teachings are not overly sensitive to any particular selections in these regards, further elaboration is not provided for the sake of brevity.

It should be understood that these teachings will readily accommodate more than two hierarchical levels, and accordingly further templates representing other hierarchical levels may be accessed when optimizing the radiation treatment plan. In some cases, at least one template representing each available hierarchical level may be accessed and utilized in these regards. In other cases, it may be useful to skip one or more hierarchical levels such that optimization proceeds without using at least one template to represent each available hierarchical level.

At optional block 203, this process 200 provides for administering radiation to the given patient using the optimized radiation treatment plan 113.

Additional details regarding these teachings will now be provided by way of some examples. It will be understood that the specific details of these examples are intended to serve an illustrative purpose and are not to be understood as suggesting any particular limitations with respect to these teachings.

Generally speaking, most or even all the initial information that defines a planning prescription for a certain planning case can divided into a class-based hierarchy. By one approach, each class in the class hierarchy has a definite meaning in the treatment planning process. For example, one class may define an overarching, facility-wide template that specifies the prescription rules and/or clinical goals for each treatment facility (such as a discrete clinic). A more specific class can provide rules and/or goals with greater granularity, such as per fractionation, or per physician, or per treatment machine workflow.

These teachings will accommodate allowing (or requiring) a given hierarchical class to inherit content from a class that is higher in the hierarchy. As noted above, such inherited information may be supplemented and/or overridden. It will be appreciated that each such class brings its own meaningful contribution to the planning process and also that each such class can be modified manually or by automatic means using artificial intelligence-based re-training models.

As one illustrative example in these regards, the initial templatized information used in planning can comprise (or constitute) rule statements (written, for example, in a format that can at the same time be understood by human experts and which can also be parsed by a plan creation algorithm, such as an optimizer) and/or models (created, for example, based on human expert-selected cases using machine learning).

There may be multiple different steps in the planning process. These teachings will accommodate providing different types of initial information for most or all of those steps. For example, the planning might start with field geometry selection. These teachings could accommodate that starting point with a list of hard-coded beam angles and/or by reference to a model that serves to predict a good isocenter location. The latter could include, for example, hard-coded rules that serve to restrict the choices that a model can consider and/or propose. To continue with this example, a second phase in planning might be an optimization process, where the initial information contains planning objectives to be used by the optimization engine to construct a utility (or cost) function. Additionally, this initial information can contain detailed instructions regarding how optimization structures are to be created or how the optimization is to be scheduled (i.e., how many iterations are performed or when to move from one optimization stage to another).

In this illustrative example the focus is not so much on how the initial information is divided amongst different process steps, but rather upon how the initial information can be sourced from different requirements. To continue the foregoing example, the final field geometry parameters could be organized as follows: the beam directions can be created based on a treatment-site hierarchical level class template (for example, for breast treatment), while the isocenter positioning model reference is specific to a particular treatment machine (and hence, for example, takes into account different physical clearances) and is therefore based on a template from a different hierarchical level class. Similarly, the plan optimization instructions could have a base-part that satisfies overall clinical protocol but there could be inherited additions related to some local outcome study, and in addition there could be a personalized template to take into account the desire of a certain oncologist to, for example, allow the optimizer to run for a longer time.

Figure 3:
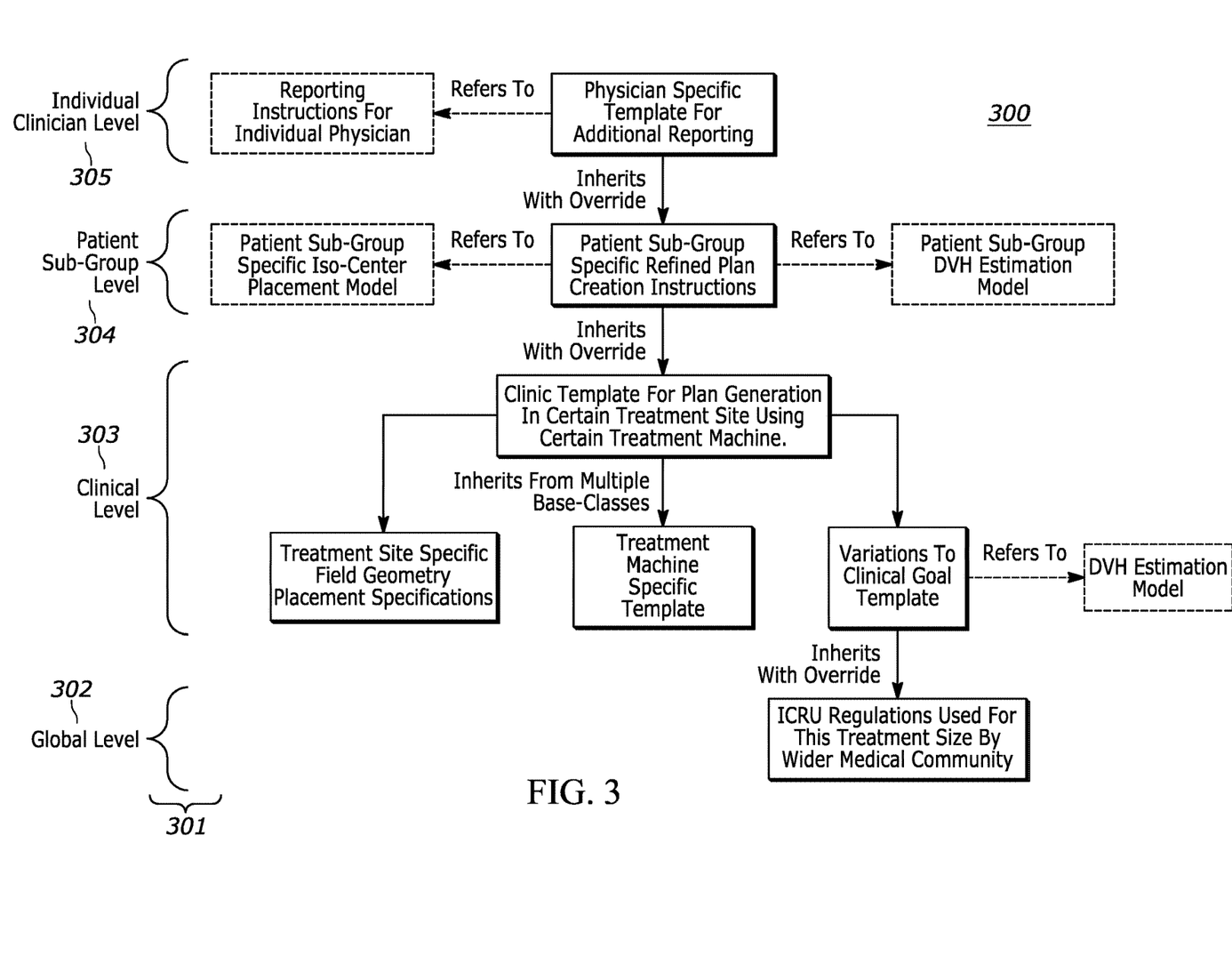
FIG. 3 comprises a chart as configured in accordance with various embodiments of these teachings.

FIG. 3 presents a more specific illustrative example in these regards. In particular, FIG. 3 presents a chart 300 depicting a set of hierarchically-diversified templates. This example presents four hierarchical classes 301 comprising a global level 302, a clinical level 303, a patient sub-group level 304, and an individual clinician level 305. Boxes with solid boundaries indicate individual classes in the hierarchy and boxes with dashed boundaries indicate rule sets or models that are referred to by the classes.

By one approach, the system facilitates inheritance and combination operations for the templates. As used herein, inheritance refers to creating a new template by inheriting the set of rules (and/or the set of references to certain models) from a template that is higher in the hierarchy and then defining a new set of rules that are either applied by way of supplementation (when there is no similar rule in the inherited class), overwriting (by replacing an inherited rule (or portion thereof) with a new one), or combination (where both the inherited and new rules are applied. By one approach, these rules can be applied in an order such that the hierarchically-higher rule is applied first and the more granular lower-level hierarchical rule is applied secondly.

By one approach, the combination approach can be similar to a straightforward inheritance approach with the exception that there are multiple different base-classes. An order can be assigned to each base-class to be used in cases where over-writing and/or a combination of individual rules is be applied.

It will be appreciated that this class-hierarchy approach can also support versioning. For example, a given template might have multiple versions thereof reflecting changes over time. The versioning can be implemented as an inheritance from an older template which would support leaving any other inherited templates intact. If desired, updating a given template can be leveraged by causing the changes to propagate to any inheriting templates. Different versions can be differentiated using, for example, a corresponding version code or the like. Also if desired, each template could have a unique identifier. Such an identifier, together with the aforementioned version information, could help provide, for example, an audit trail to facilitate determining the instructions that were actually used for planning purposes in a given instance.

A rule-level combination of contradicting or overlapping rules can be facilitated in various ways. For example, by one approach, and when effecting a pure replacement, the contradicting rules can be detected by the control circuit 101 and the rule in the latter order of appearance is applied to overwrite the original rule (that appeared in the higher hierarchical level template). The contradiction can be recognized as a merge-conflict between the old and new rule. As an example, the base-class might have a certain clinical goal defined as part of the instructions for the optimizer while the additional set of rules used in the inheritance lists the same clinical goal but with a different priority. The preferred action can be to replace the old priority (from the higher-level hierarchical class) with the new priority (from the lower-level hierarchical class).

As another example, when effecting a rule-combination, both (or all) rules are retained in the inherited template. The more precise rule can be applied first, with any more generic rules being applied as a constraint. As an example, the base-class template might define a certain model to be used to create a start and stop angle for a volumetric modulated arc therapy treatment process and the inheritance template can then add a rules that specify boundaries for accepted angles. The combination of the rules results in first running the model and then doing any necessary modifications if the solution falls outside of the acceptable interval specified in the first set.

By one approach, the control circuit 101, when managing inheritances, can be configured to resolve conflicts amongst rules being inherited and/or applied in a hierarchically stepped manner. The control circuit 101 can also facilitate any access control or staging of the templates based on which versions are accepted for clinical use. It would also be possible to include management of validation cases to support automatic testing of proposed changes in the templates.

The proposed class-hierarchy approach makes it easy to create and refine models that only concentrate and/or apply in specific localized places in the planning process. For example, an artificial intelligence model can be created that only addresses the planning aspects of a certain user and acts only as a source of supplementary information to the more general class template.

Figure 4:
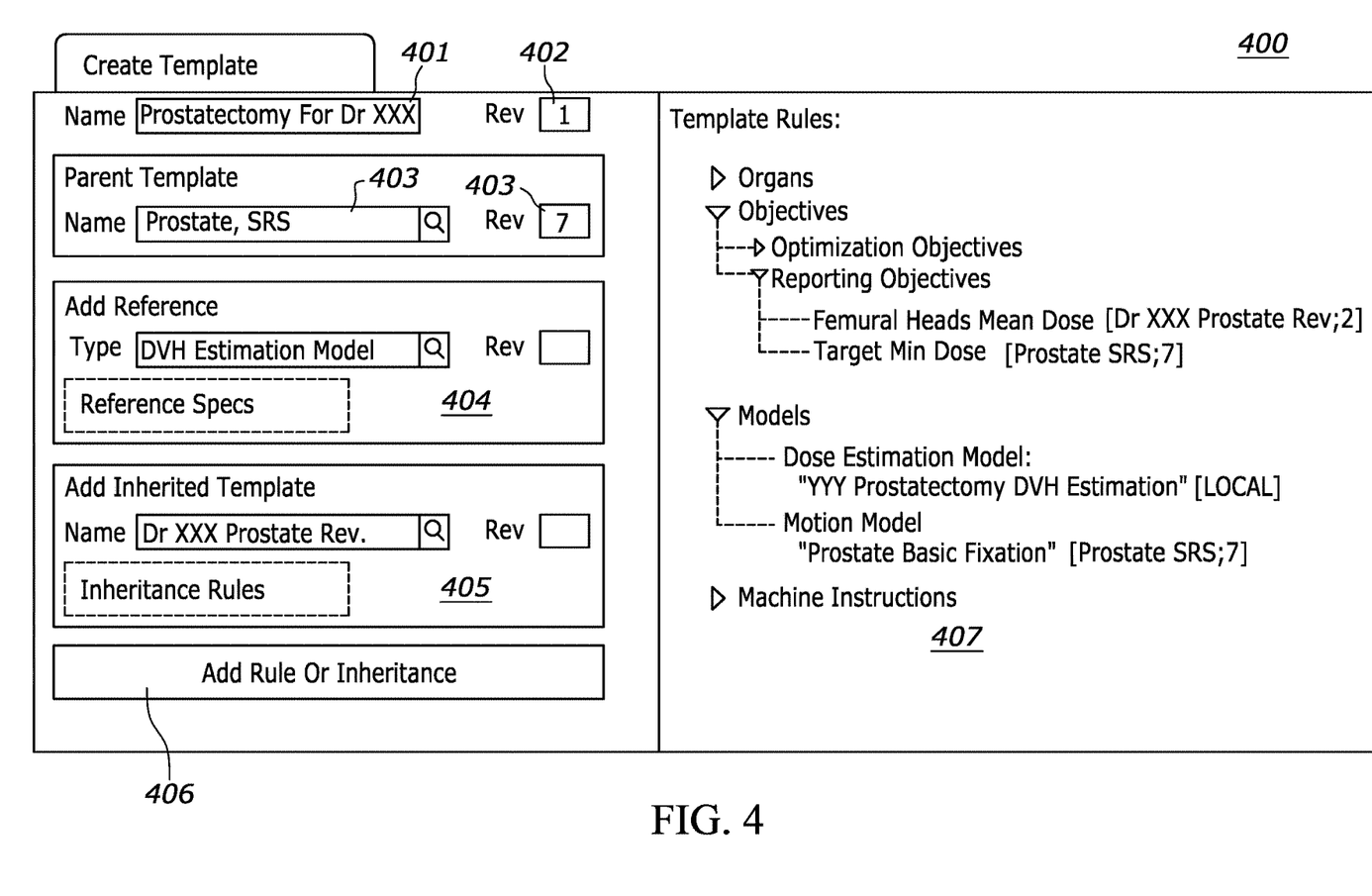
FIG. 4 comprises a screen shot as configured in accordance with various embodiments of these teachings.

FIG. 4 presents a screenshot 400 for an illustrative example of a template creation tool as presented, for example, by the control circuit 101 via the aforementioned user interface 103.

A first field 401 provides an area where the user can enter a name for the new template. A second related field 402 provides an opportunity to denote and track revisions to this particular template.

A parent template selection box (with a corresponding revision selection box) 403 permits the user to select a particular template from a higher level in the hierarchy to select as a parent template. The user can enter text and click on the search icon to locate the desired parent template. These teachings would also accommodate allowing the user to pull up a window that presents all available templates from which the user can make their selection. By one approach, upon selecting a particular revision number, this new template will not be automatically changed should future changes be made to the parent template—instead, the selection revision will continue to serve as the parent template.

Reference numeral 404 denotes an area where new and/or overriding rules can be added to the template. This is done in this illustrative example by providing the user with an opportunity to select a particular reference (with a field being included to permit the user to identify the type of reference to be added). Additional parameters that might be needed by the added reference can be filled in by accessing a dialog mechanism that opens upon asserting the "reference specs" button.

At the area denoted by reference numeral 405, the user is provided with an opportunity to add an inherited template. In this illustrative example, this area permits the user to add templates beyond the "parent" template described above. A mechanism is provided to allow the user to specify rules regarding how to handle conflicting rules amongst the various parent/inherited templates (in particular, for example, which templates override which other templates). The application of such rules may depend, for example, upon the order in which the added components (i.e., templates and references) are presented and/or selected, which may correlate to a default situation of preferring a last-entered selection.

Note that, in the foregoing area 405, the field for revisions is blank. In this case, the new template will always use a most current version of the inherited template, as versus any specifically identified revision.

The button denoted by reference numeral 406 permits the user to add additional rules or inheritances if they so wish.

The area denoted by reference numeral 407 sets forth the rules for the new template. It can be seen that the new template constitutes a generated knowledge template in that it is created based on the locally defined references and/or content inherited from the parent template(s). As illustrated, these rules can be annotated to indicate the source for a given rule (where the source can be identified, for example, using the name of the source template or an expression such as "local" to indicate that this particular rule is of local definition).

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method to facilitate planning a radiation treatment plan for a given patient at a given radiation treatment facility, the method comprising:
by a control circuit:
accessing a memory having stored therein a plurality of hierarchically-diversified radiation treatment planning templates that include:
at least a first radiation treatment planning template specifying radiation treatment planning information at a first hierarchical level; and
at least a second radiation treatment planning template specifying radiation treatment planning information at a second hierarchical level, wherein the second hierarchical level is more granular than the first hierarchical level; and
optimizing a radiation treatment plan for the given patient using the given radiation treatment facility as a function of at least the first and the second radiation treatment planning template.

2. The method of claim 1 wherein at least some of the hierarchical levels correspond to sequentially different steps in planning the radiation treatment plan.

3. The method of claim 2 wherein at least one of the sequentially different steps comprises a field geometry selection step and wherein at least another of the sequentially different steps comprises an iterative radiation treatment plan optimization step.

4. The method of claim 1 wherein the first hierarchical level corresponds to universally-applied specifications for the given radiation treatment facility and wherein the second hierarchical level corresponds to specifications that are not universally applied for the given radiation treatment facility.

5. The method of claim 1 wherein the second radiation treatment planning template corresponds to specifications as per one of:
per fractionation;
per prescribing physician;
per radiation treatment machine planning workflow.

6. The method of claim 1 wherein the radiation treatment planning information for each of the first and second hierarchical levels comprises initial planning information corresponding to planning the radiation treatment plan.

7. The method of claim 1 wherein the second radiation treatment planning template includes information that is identical to information in the first radiation treatment planning template.

8. The method of claim 1 wherein the second radiation treatment planning template includes information that supplements information in the first radiation treatment planning template.

9. The method of claim 1 wherein the second radiation treatment planning template includes information that overrides information in the first radiation treatment planning template.

10. The method of claim 1 wherein accessing the memory having stored therein the plurality of hierarchically-diversified radiation treatment planning templates comprises accessing a plurality of differing ones of the second radiation treatment planning templates that each specify radiation treatment planning information at the second hierarchical level.

11. An apparatus to facilitate planning a radiation treatment plan for a given patient at a given radiation treatment facility, the apparatus comprising:
a memory having stored therein a plurality of hierarchically-diversified radiation treatment planning templates that include:
at least a first radiation treatment planning template specifying radiation treatment planning information at a first hierarchical level; and
at least a second radiation treatment planning template specifying radiation treatment planning information at a second hierarchical level, wherein the second hierarchical level is more granular than the first hierarchical level; and
a control circuit configured to access the memory and to optimize a radiation treatment plan for the given patient using the given radiation treatment facility as a function of at least the first and the second radiation treatment planning template.

12. The apparatus of claim 11 wherein at least some of the hierarchical levels correspond to sequentially different steps in planning the radiation treatment plan.

13. The apparatus of claim 12 wherein at least one of the sequentially different steps comprises a field geometry selection step and wherein at least another of the sequentially different steps comprises an iterative radiation treatment plan optimization step.

14. The apparatus of claim 11 wherein the first hierarchical level corresponds to universally-applied specifications for the given radiation treatment facility and wherein the second hierarchical level corresponds to specifications that are not universally applied for the given radiation treatment facility.

15. The apparatus of claim 11 wherein the second radiation treatment planning template corresponds to specifications as per one of:
per fractionation;
per prescribing physician;
per radiation treatment machine planning workflow.

16. The apparatus of claim 11 wherein the radiation treatment planning information for each of the first and second hierarchical levels comprises initial planning information corresponding to planning the radiation treatment plan.

17. The apparatus of claim 11 wherein the second radiation treatment planning template includes information that is identical to information in the first radiation treatment planning template.

18. The apparatus of claim 11 wherein the second radiation treatment planning template includes information that supplements information in the first radiation treatment planning template.

19. The apparatus of claim 11 wherein the second radiation treatment planning template includes information that overrides information in the first radiation treatment planning template.

20. The apparatus of claim 11 wherein the control circuit is configured to access the memory having stored therein the plurality of hierarchically-diversified radiation treatment planning templates by accessing a plurality of differing ones of the second radiation treatment planning templates that each specify radiation treatment planning information at the second hierarchical level.

* * * * *